(12) United States Patent
Elsheikhy et al.

(10) Patent No.: US 9,643,889 B1
(45) Date of Patent: May 9, 2017

(54) METHOD OF STORING EXFOLIATED NANOCLAY PARTICLES

(71) Applicant: KING SAUD UNIVERSITY, Riyadh (SA)

(72) Inventors: Refat Ahmed Ibrahim Elsheikhy, Riyadh (SA); Mosleh Ali Alshamrani, Riyadh (SA)

(73) Assignee: KING SAUD UNIVERSITY, Riyadh (SA)

(*) Notice: Subject to any disclaimer, the term of this patent is extended or adjusted under 35 U.S.C. 154(b) by 0 days.

(21) Appl. No.: 15/094,998

(22) Filed: Apr. 8, 2016

(51) Int. Cl.
*C04B 33/04* (2006.01)
*G01N 23/00* (2006.01)
*H01J 37/28* (2006.01)

(52) U.S. Cl.
CPC ............. *C04B 33/04* (2013.01); *G01N 23/00* (2013.01); *C04B 2235/349* (2013.01); *H01J 37/28* (2013.01)

(58) Field of Classification Search
CPC ...................................................... C04B 33/04
See application file for complete search history.

(56) References Cited

U.S. PATENT DOCUMENTS

| | | | |
|---|---|---|---|
| 6,454,974 B1* | 9/2002 | Wilson | B29C 44/146 264/250 |
| 6,943,206 B2 | 9/2005 | Haraguchi | |
| 7,528,191 B2 | 5/2009 | Metzemacher et al. | |
| 8,278,383 B2 | 10/2012 | Chan et al. | |
| 8,828,288 B2 | 9/2014 | Liao et al. | |
| 2005/0191490 A1* | 9/2005 | Ton-That | B82Y 30/00 428/407 |
| 2007/0173598 A1* | 7/2007 | Williams | B82Y 30/00 524/588 |
| 2009/0018229 A1* | 1/2009 | Sogah | B82Y 30/00 522/51 |
| 2014/0158020 A1 | 6/2014 | Wegst et al. | |
| 2016/0194536 A1* | 7/2016 | Natori | C09K 3/1006 277/650 |

FOREIGN PATENT DOCUMENTS

| | | | | |
|---|---|---|---|---|
| CN | 102268140 B | * | 12/2012 | |
| JP | WO 2015015737 A1 | * | 2/2015 | ........... C09K 3/1006 |
| WO | WO 2005/068364 A1 | | 7/2005 | |

* cited by examiner

*Primary Examiner* — Melvin C Mayes
*Assistant Examiner* — James Corno
(74) *Attorney, Agent, or Firm* — Richard C. Litman

(57) ABSTRACT

The method of storing exfoliated nanoclay particles involves the freezing of exfoliated nanoclay particles in water, thus forming ice with the exfoliated nanoclay particles suspended therein. The frozen state of the suspension prevents the exfoliated nanoclay particles from agglomerating, thus allowing the nanoclay particles to be stored and transported while maintaining their exfoliated state. The exfoliated nanoclay particles are added to the water to form a suspension, and the suspension is then mixed for between 24 and 72 hours to ensure that no agglomerated nanoclay particles are in suspension and that the suspension contains only exfoliated nanoclay particles. The suspension is then frozen to store the exfoliated nanoclay particles in ice.

6 Claims, No Drawings

METHOD OF STORING EXFOLIATED NANOCLAY PARTICLES

BACKGROUND OF THE INVENTION

1. Field of the Invention

The present invention relates to clay nanoparticles, and particularly to a method of storing exfoliated nanoclay particles to prevent agglomeration thereof.

2. Description of the Related Art

Phyllosilicates, such as montmorillonite, kaolinite, halloysite, and the like, are clays with a wide variety of uses, particularly in their nanoparticle forms (i.e., nanoclays). Such nanoclays are used in the oil industry, in the medical and pharmaceutical industries, and a wide variety of other industries. Nanoclays have a wide variety of desirable properties, making them useful as flocculants, catalysts, anti-caking agents and more.

In their natural state, phyllosilicate clays clump or agglomerate into macro-scale particles. Nanoclays are typically produced from the larger scale clay particles by a process known as exfoliation, which separates the agglomerated particles, layer by layer, into individual clay layers or platelets. A typical method of exfoliation involves the use of a high shear mixer at high speed. However, the exfoliated nanoclay particles tend to re-agglomerate, particularly when held in liquid suspension or solution. Thus, when stored and/or transported, the re-agglomerated nanoparticles must once again be exfoliated. Such exfoliation must be performed again and again, prior to the application of the exfoliated nanoclay particles. Thus, a method of storing exfoliated nanoclay particles solving the aforementioned problems is desired.

SUMMARY OF THE INVENTION

The method of storing exfoliated nanoclay particles involves the freezing of exfoliated nanoclay particles in water, thus forming ice with the exfoliated nanoclay particles suspended therein. The frozen state of the suspension prevents the exfoliated nanoclay particles from agglomerating, thus allowing the nanoclay particles to be stored and transported while maintaining their exfoliated state.

The exfoliated nanoclay particles are added to the water to form a suspension, and the suspension is then mixed for between 24 and 72 hours to ensure that no agglomerated nanoclay particles are in suspension and that the suspension contains only exfoliated nanoclay particles. A sample of the suspension may be examined by a scanning electron microscope (SEM) or the like to ensure that the suspension contains pure exfoliated nanoclay particles with no agglomeration. The suspension is then frozen to store the exfoliated nanoclay particles in ice. The suspension may be poured into a mold or tray to form the stored exfoliated nanoclay particles into ice cubes or the like, similar to the formation and storage of ice cubes in conventional ice cube trays.

It should be understood that the method of storing exfoliated nanoclay particles may be used for any suitable type of nanoclay, such as montmorillonite nanoclay, kaolinite nanoclay, halloysite nanoclay or the like. Further, it should be understood that as an alternative to freezing, the exfoliated nanoclay particles may be stored in a liquid suspension, which may be held in cans, bottles, tanks or the like.

These and other features of the present invention will become readily apparent upon further review of the following specification.

DETAILED DESCRIPTION OF THE PREFERRED EMBODIMENTS

The method of storing exfoliated nanoclay particles involves the freezing of exfoliated nanoclay particles in water, thus forming ice with the exfoliated nanoclay particles suspended therein. The frozen state of the suspension prevents the exfoliated nanoclay particles from agglomerating, thus allowing the nanoclay particles to be stored and transported while maintaining their exfoliated state, specifically in the form of nanoclay platelets or layers.

The exfoliated nanoclay particles are added to the water to form a suspension, and the suspension is then mixed for between 24 and 72 hours to ensure that no agglomerated nanoclay particles are in suspension and that the suspension contains only exfoliated nanoclay particles. Preferably, the exfoliated nanoclay particles are added to deionized or distilled water. Mixing may be performed by a conventional rotating mixer, a high shear mixer, or the like. The mixing of the particles in the water at high speed ensures exfoliation of the bonded nanoclay layers by breaking the bi-interfacial bond between adjacent layers, thus freeing each layer to form exfoliated layers or platelets.

A sample of the suspension may be examined by a scanning electron microscope (SEM) or the like to ensure that the suspension contains pure exfoliated nanoclay particles with no agglomeration. The suspension is then frozen to store the exfoliated nanoclay particles in water ice. The suspension may be poured into a mold or tray to form the stored exfoliated nanoclay particles into ice cubes or the like, similar to the formation and storage of ice cubes in conventional ice cube trays.

It should be understood that the method of storing exfoliated nanoclay particles may be used for any suitable type of nanoclay, such as, montmorillonite nanoclay, kaolinite nanoclay, halloysite nanoclay, or the like. Further, it should be understood that as an alternative to freezing, the exfoliated nanoclay particles may be stored in a liquid suspension, which may be held in cans, bottles, tanks or the like.

It should be further understood that the exfoliated nanoclay particles may be provided by any suitable process. For example, a conventional mechanical process may be used, such as exfoliation of nanoclay particles with a high shear mixer. Preferably, prior to forming the suspension of the exfoliated nanoclay particles, a sample of the exfoliated nanoclay particles is tested by scanning electron microscope (SEM) or the like to ensure purity of the exfoliated state.

It is to be understood that the present invention is not limited to the embodiments described above, but encompasses any and all embodiments within the scope of the following claims.

We claim:

1. A method of storing exfoliated nanoclay particles in ice cubes, the steps consist of:
    adding exfoliated nanoclay particles to water to form a suspension;
    mixing the suspension, wherein the step of mixing is for a period between 24 and 72 hours to ensure that no agglomerated nanoclay particles are in the suspension;
    pouring the suspension into an ice cube mold, wherein the suspension contains only exfoliated nanoclay particles with no agglomeration; and
    freezing the water to store the exfoliated nanoclay particles in the ice cube mold without agglomeration.

2. The method of storing exfoliated nanoclay particles as recited in claim 1, wherein the step of adding the exfoliated nanoclay particles to the water comprises adding exfoliated montmorillonite nanoclay particles to water.

3. The method of storing exfoliated nanoclay particles as recited in claim 1, wherein the step of adding the exfoliated nanoclay particles to the water comprises adding exfoliated kaolinite nanoclay particles to water.

4. The method of storing exfoliated nanoclay particles as recited in claim 1, wherein the step of adding the exfoliated nanoclay particles to the water comprises adding exfoliated halloysite nanoclay particles to water.

5. The method of storing exfoliated nanoclay particles as recited in claim 1, wherein said step of mixing the suspension comprises mixing the suspension of exfoliated nanoclay particles in water in a high-speed shear mixer for between 24 and 72 hours.

6. The method of storing exfoliated nanoclay particles as recited in claim 1, wherein the water is selected from the group consisting of deionized and distilled water.

* * * * *